United States Patent
Brinkmann et al.

(10) Patent No.: US 12,171,436 B2
(45) Date of Patent: *Dec. 24, 2024

(54) OCCLUDER DEVICES

(71) Applicant: W. L. Gore & Associates, Inc., Newark, DE (US)

(72) Inventors: John M. Brinkmann, Flagstaff, AZ (US); Paul D. Goodman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 104 days.

This patent is subject to a terminal disclaimer.

(21) Appl. No.: 18/088,183

(22) Filed: Dec. 23, 2022

(65) Prior Publication Data

US 2023/0131277 A1    Apr. 27, 2023

Related U.S. Application Data

(63) Continuation of application No. 17/053,421, filed as application No. PCT/US2019/028744 on Apr. 23, 2019, now Pat. No. 11,564,693.

(60) Provisional application No. 62/668,505, filed on May 8, 2018.

(51) Int. Cl.
   *A61B 17/12*    (2006.01)
(52) U.S. Cl.
   CPC .......... *A61B 17/12136* (2013.01); *A61B 2017/12054* (2013.01); *A61B 17/12109* (2013.01)
(58) Field of Classification Search
   CPC .......... A61B 17/12136; A61B 2017/12054
   See application file for complete search history.

(56) References Cited

U.S. PATENT DOCUMENTS

| | | |
|---|---|---|
| 5,382,261 A | 1/1995 | Palmaz |
| 5,941,896 A | 8/1999 | Kerr |
| 6,254,633 B1 | 7/2001 | Pinchuk et al. |
| 6,589,263 B1 | 7/2003 | Hopkins et al. |
| 6,702,834 B1 | 3/2004 | Boylan et al. |
| 7,604,650 B2 | 10/2009 | Bergheim |
| 8,948,848 B2 | 2/2015 | Merhi |
| 9,232,992 B2 | 1/2016 | Heidner et al. |
| 2001/0012951 A1 | 8/2001 | Bates et al. |
| 2002/0022860 A1 | 2/2002 | Borillo et al. |
| 2003/0069596 A1 | 4/2003 | Eskuri |

(Continued)

FOREIGN PATENT DOCUMENTS

| | | |
|---|---|---|
| WO | 2003/077984 A1 | 9/2003 |
| WO | 2005/011535 A2 | 2/2005 |

(Continued)

OTHER PUBLICATIONS

International Preliminary Report on Patentability received for PCT Patent Application No. PCT/US2019/028744, mailed on Nov. 19, 2020, 9 pages.

(Continued)

*Primary Examiner* — Phong Son H Dang

(57) ABSTRACT

Various aspects of the present disclosure are directed toward systems, methods, and apparatuses that include an occlusion device having a barrier member. The barrier member may include an enlargeable portion and a tail portion extending from the enlargeable portion. The enlargeable portion and the tail portion are releasably coupled to the delivery catheter such that the tail portion is radially unsupported and collapsible upon deployment.

21 Claims, 12 Drawing Sheets

(56) References Cited

U.S. PATENT DOCUMENTS

| | | |
|---|---|---|
| 2003/0077984 A1 | 4/2003 | Smith et al. |
| 2003/0212429 A1 | 11/2003 | Keegan et al. |
| 2003/0229366 A1 | 12/2003 | Reggie et al. |
| 2004/0093012 A1 | 5/2004 | Cully et al. |
| 2006/0223386 A1 | 10/2006 | Pal |
| 2006/0265052 A1 | 11/2006 | You |
| 2007/0038241 A1 | 2/2007 | Pal |
| 2012/0041550 A1 | 2/2012 | Salahieh et al. |
| 2012/0130468 A1 | 5/2012 | Khosravi et al. |
| 2013/0184658 A1 | 7/2013 | Duncan |
| 2013/0261731 A1 | 10/2013 | Zhou et al. |
| 2014/0005540 A1 | 1/2014 | Merhi |
| 2014/0031924 A1 | 1/2014 | Bruchman et al. |
| 2014/0364941 A1 | 12/2014 | Edmiston et al. |
| 2015/0039017 A1 | 2/2015 | Cragg et al. |
| 2016/0310152 A1 | 10/2016 | Sepetka et al. |
| 2018/0360432 A1 | 12/2018 | Corcoran et al. |
| 2021/0228216 A1 | 7/2021 | Brinkmann et al. |
| 2022/0280753 A1 | 9/2022 | Garrison et al. |

FOREIGN PATENT DOCUMENTS

| | | |
|---|---|---|
| WO | 2006/127756 A2 | 11/2006 |
| WO | 2019/217069 A1 | 11/2019 |

OTHER PUBLICATIONS

International Search Report and Written Opinion received for PCT Patent Application No. PCT/US2019/028744, mailed on Aug. 27, 2019, 13 pages.

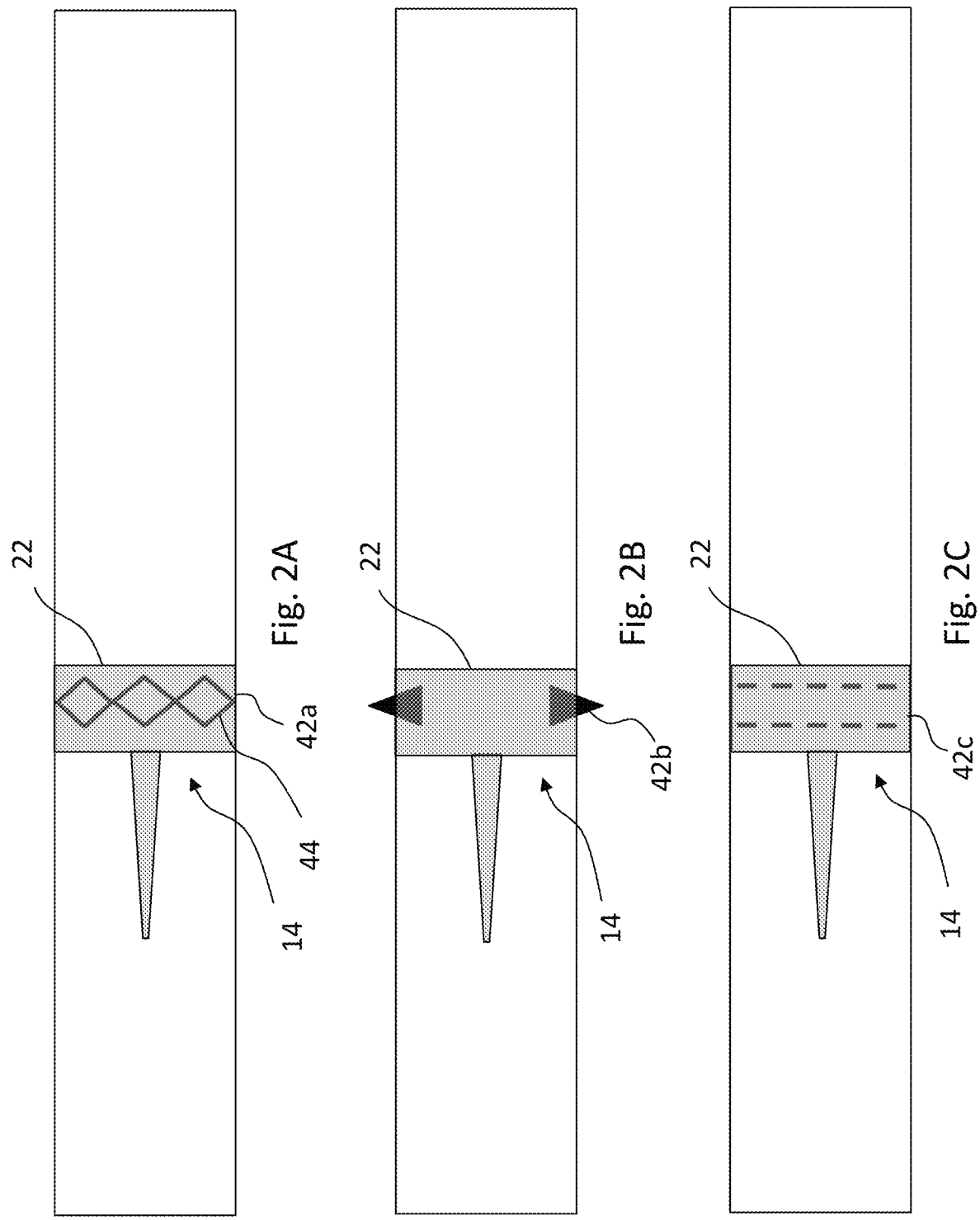

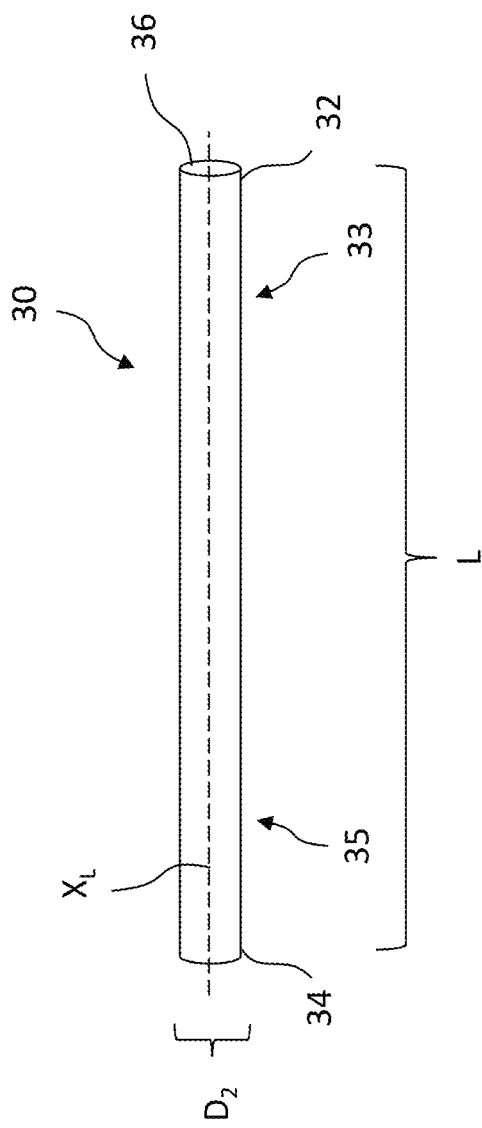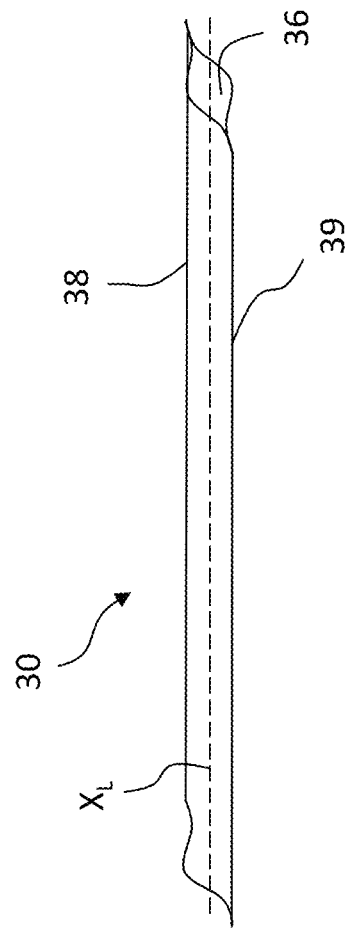
Fig. 3A
Fig. 3B

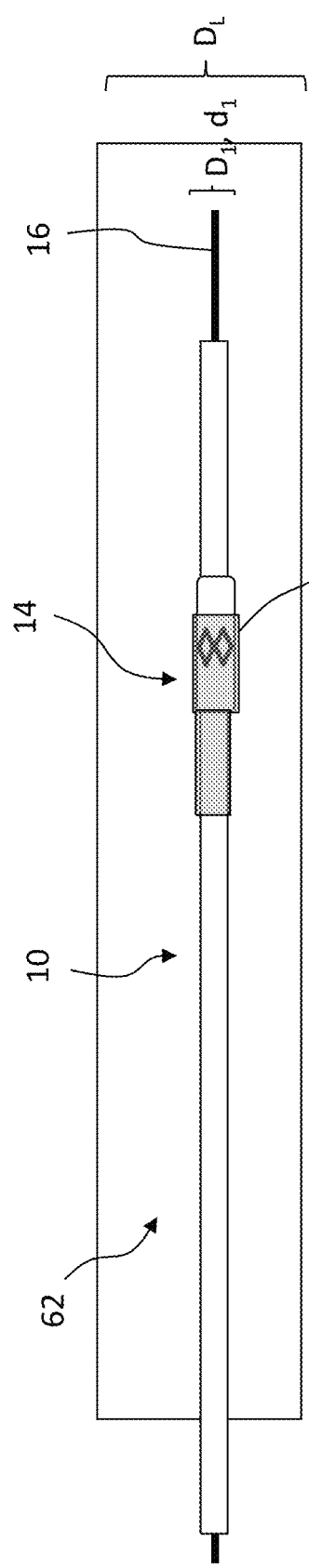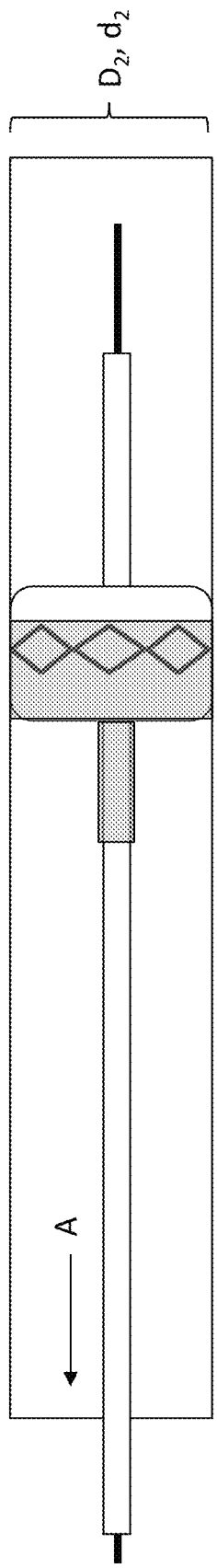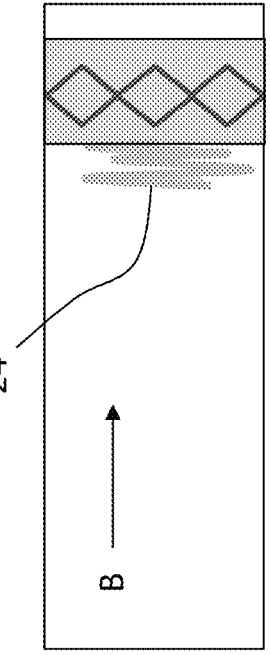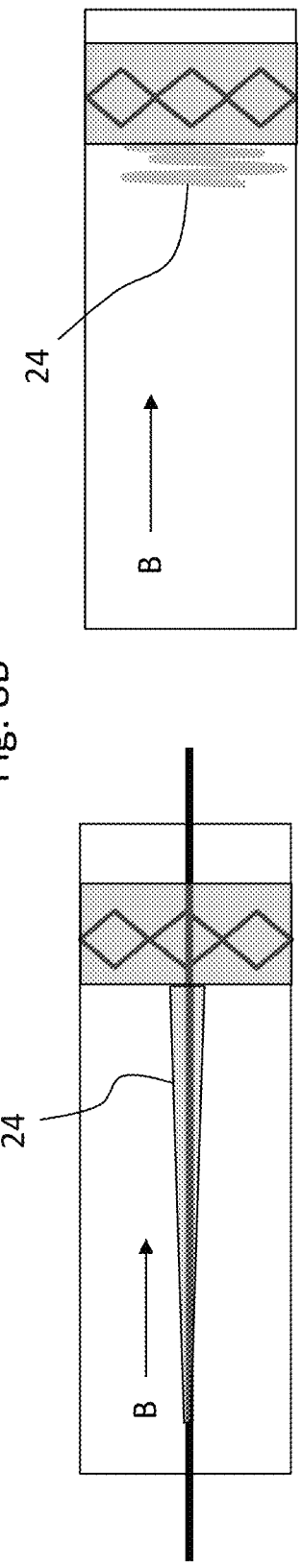

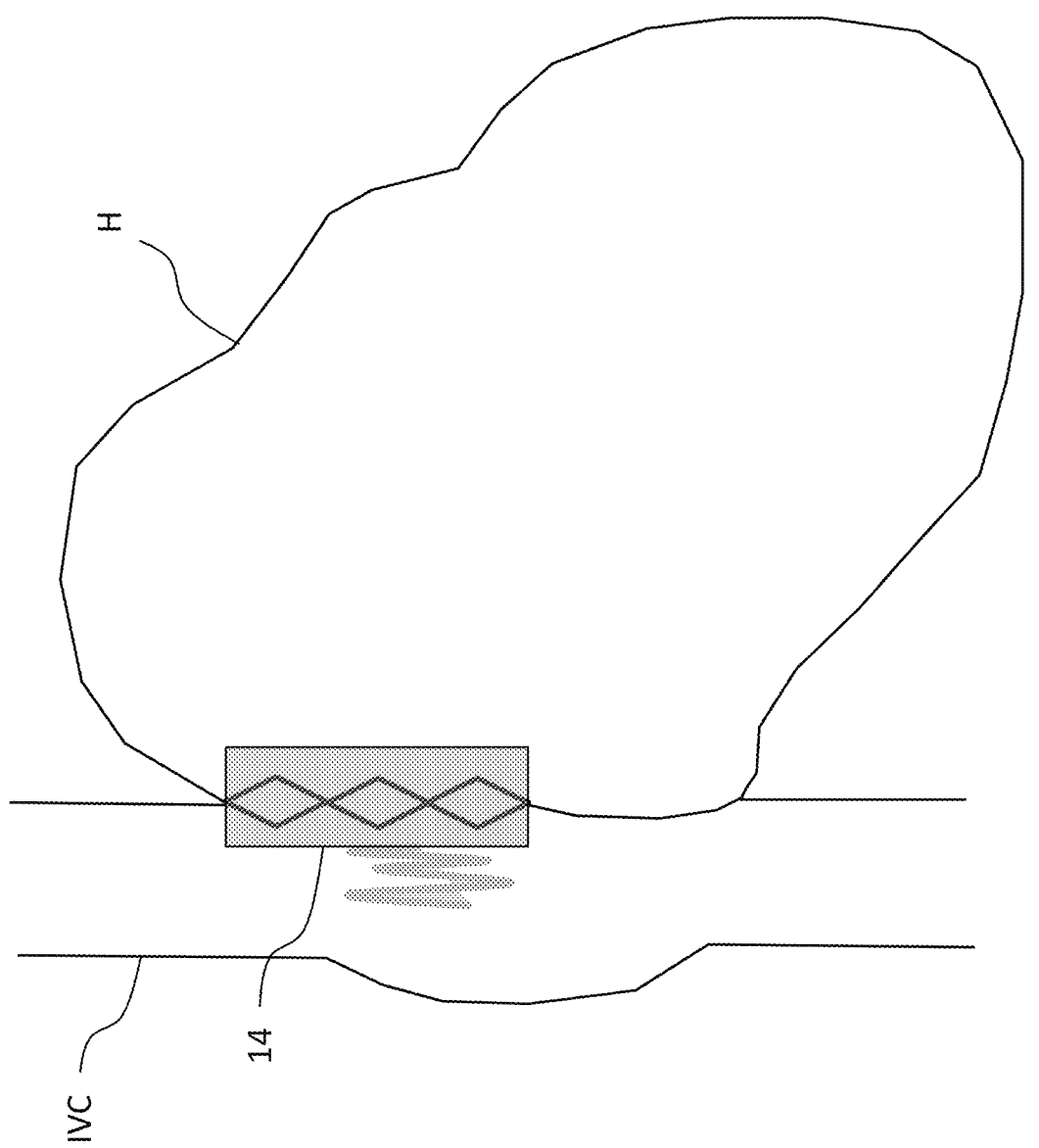

OCCLUDER DEVICES

CROSS-REFERENCE TO RELATED APPLICATION

This application is a continuation of U.S. application Ser. No. 17/053,421, filed Nov. 6, 2020, which is a national phase application of PCT Application No. PCT/US2019/028744, internationally filed on Apr. 23, 2019, which claims the benefit of Provisional Application No. 62/668,505, filed May 8, 2018, which are incorporated herein by reference in their entirety entireties for all purposes.

FIELD

The present disclosure relates generally to implantable medical devices, and more specifically to implantable medical devices for occluding, inhibiting, or preventing material movement and/or fluid flow through tissue apertures or body lumens.

BACKGROUND

Endovascular embolization is a treatment for various diseases and conditions in which blood vessels or other vascular channels and body lumens are malformed, distended, and/or ruptured. Examples of such conditions include aneurysms, arteriovenous malformations, and certain oncological conditions, among others. Embolization can involve occluding or blocking the malformed regions or passageways to prevent blood flow to certain areas of the body such as, for example, a tumor or an aneurysm. In some examples, a certain vessel or passageway may be occluded to force and/or increase fluid flow through an adjacent vessel.

A number of occluding devices exist for the treatment of such conditions, some of which include coils, balloons, foam, plugs, and others. Such devices generally cut off blood supply to the affected area.

SUMMARY

Various examples relate to implantable medical devices and systems for occluding, inhibiting, or preventing material movement and/or fluid flow through tissue apertures or body lumens. In particular, various examples relate to an occlusion device or system including a barrier member having an enlargeable portion, an anchor feature, and a collapsible tail portion.

According to one example ("Example 1"), an occlusion system includes a delivery catheter. The delivery catheter has a proximal end, a distal end, a proximal portion, and a distal portion. The occlusion system also includes an occlusion device coupled to the delivery catheter. The occlusion device is in a reduced profile delivery configuration. The occlusion device includes a barrier member including a radially enlargeable portion, a tail portion extending from the enlargeable portion, an anchor feature arranged with the enlargeable portion of the barrier member, and a lumen. The lumen extends through the enlargeable portion and the anchor portion and is configured to receive the delivery catheter. The enlargeable portion and the tail portion are releasably coupled to the catheter such that the tail portion is radially unsupported and collapsible upon deployment from the delivery catheter.

According to another example ("Example 2") further to Example 1, the anchor feature includes a support member coupled to the enlargeable portion of the barrier member. The support member is expandable from a delivery configuration to a deployed configuration.

According to another example ("Example 3") further to any one of Examples 1 to 2, the tail portion of the barrier member is configured to be released from the delivery catheter upon application of a retraction force to the tail portion with the catheter.

According to another example ("Example 4") further to any one of Examples 1 to 3, the tail portion is configured to plastically deform and neck down in diameter upon application of the retraction force on the tail portion prior to release of the tail portion from the catheter.

According to another example ("Example 5") further to any one of Examples 1 to 4, the tail portion includes opposing, longitudinal creases configured to facilitate radial collapsing of the tail portion following release from the catheter.

According to another example ("Example 6") further to any one of Examples 1 to 5, the tail portion is adhered to the catheter.

According to another example ("Example 7") further to any one of Examples 1 to 6, the tail portion is formed of an elastomeric material. The tail portion is configured to constrict following release from the delivery catheter.

According to another example ("Example 8") further to any one of Examples 1 to 7, a ratio of the outer diameter of the barrier member to the length of the barrier member is at least 1 to 10.

According to another example ("Example 9") further to any one of Examples 1 to 8, the tail portion is configured to evert through the enlargeable portion during retraction of the catheter following deployment of the enlargeable portion.

According to another example ("Example 10") further to any one of Examples 1 to 9, the anchor feature includes at least one of: adhesive, one or more barbs, and an expandable framework.

According to another example ("Example 11") further to any one of Examples 1 to 10, the system also includes a balloon. The balloon is configured to expand the enlargeable portion from the delivery configuration to the deployed configuration upon inflation of the balloon.

According to another example ("Example 12") further to any one of Examples 1 to 11, the system also includes a constraint. The constraint is configured to prevent expansion of the enlargeable portion prior to deployment.

According to another example ("Example 13"), an implantable medical device includes a barrier member. The barrier member includes a first end, a second end, an enlargeable portion configured to expand from a delivery configuration to a deployed configuration, a tail portion, a lumen extending from the first end to the second end, a length, and an outer diameter. The tail portion is configured to flatten against itself to form a seal. The implantable medical device also includes an anchor feature coupled to the barrier member at the enlargeable portion. The anchor feature is configured to expand with the barrier member from the delivery configuration to the deployed configuration.

According to another example ("Example 14") further to Example 13, a ratio of the outer diameter of the barrier member to the length of the barrier member is at least 1 to 10.

According to another example ("Example 15") further to any one of Examples 13 to 14, the anchor feature includes at least one of: adhesive, one or more barbs, and an expandable framework.

According to another example (Example 16") further to any one of Examples 13 to 15, the anchor feature includes a support member. The support member has an expandable framework.

According to another example ("Example 17") further to any one of Examples 13 to 16, the first end and the second end of the barrier member are substantially open while the enlargeable portion is in the delivery configuration.

According to another example ("Example 18") further to any one of Examples 13 to 17, the second end of the barrier member is substantially closed while the enlargeable portion is in the deployed configuration.

According to another example ("Example 19") further to any one of Examples 13 to 18, the tail portion of the barrier member is configured to evert upon expansion of the enlargeable portion to the deployed configuration.

According to another example ("Example 20"), a method of delivering an implantable medical device includes intraluminally delivering the system of any one of Examples 1 to 12 to a desired treatment site within a body lumen of a patient. The method also includes expanding the enlargeable portion of the barrier member to fit the body lumen.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIGS. 2A-2C show various examples of anchor features, according to some embodiments;

FIGS. 3A-3B show various examples of barrier members, according to some embodiments;

FIGS. 8A-8D show another method of delivery an implantable occlusion device to a body lumen of a patient, according to some embodiments;

FIG. 9 is an example of an occlusion device employed within a body lumen of a patient, according to some embodiments;

Figure 1A:
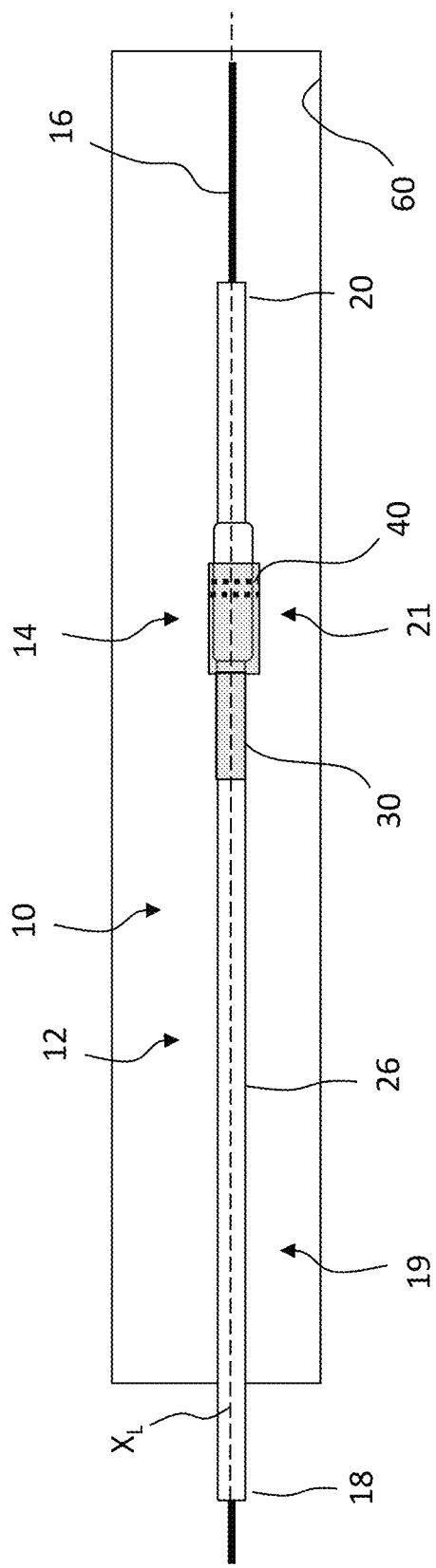
FIG. 1A shows a profile of an occlusion system in a delivery configuration, according to some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Various aspects of the present disclosure relate to designs for implantable medical devices for occluding body lumens such as vasculature of a patient. The devices can be configured for partial (e.g., restricted flow), selective (e.g., valved flow), and/or total occlusion as desired. The term "occlusion," as used herein, includes the partial, selective, and total occlusion. In addition, various aspects of the present disclosure relate to occlusion systems for occlusive treatment at a desired treatment location within the body of a patient, such as a body lumen of a patient. For reference, the term "body lumen" should be read to include any passage within the body of a patient that is capable of occlusion. In some examples, the occlusion system may include a delivery catheter and an occlusion device. The occlusion device may be self-expanding, expandable by application of an expansion force, or combinations thereof.

In certain instances, it may be beneficial to seal the body lumen rapidly and efficiently such as, for example, in large or high-flow vascular channels, to prevent further damage to the area or undesirable effects to the patient. Occlusion systems, according to the examples provided herein, can be advantageous in several respects, including the ability to be produced using efficient manufacturing processes and provide fast, secure, and reliable occlusion by effectuating device closure/sealing in response to the natural body pressure (e.g., blood pressure) within the body lumen.

In some examples, the occlusion systems discussed herein can also treat a wide range of body passages with a single device. In some examples, the occlusion systems permit guidewire access through both ends of the occlusion device without compromising luminal sealing, causing an inflow of bodily fluid, or otherwise interfering with efficacy. In some examples, the system permits one or more guidewires to remain in place during device delivery, after device delivery, and/or during and after occlusion device removal from the patient's body, reducing and/or eliminating the need for multiple devices and/or procedures.

FIG. 1A shows an occlusion system 10 including a delivery catheter 12, an occlusion device 14, and an optional guidewire 16 in a delivery configuration. The delivery catheter 12 is configured for delivering the occlusion device 14 to a desired location in a body of a patient. Examples of body passages in which the system 10 is employable include arteries, veins, airways, the gastrointestinal tract, the urinary tract, the biliary tract, left atrial appendages, walls of the heart, shunts, and other body passages, whether naturally or artificially formed.

As shown in FIG. 1A, in some embodiments, the delivery catheter 12 has a proximal end 18, a distal end 20, a central longitudinal axis XL, a proximal portion 19 near the proximal end 18, and a distal portion 21 near the distal end 20. The delivery catheter 12 has a length suitable to reach a desired treatment location within the body of a patient for delivery of the device 14 to the desired treatment location. For example, the delivery catheter 12 may have a length from about 80 cm to about 140 cm. However, it should be understood that the delivery catheter 12 can have any length as desired depending on a variety of factors, including the desired treatment location. Although endoluminal delivery methods are generally described in association with the occlusion system 10, the occlusion system 10 may also be used in laparoscopic methods and other surgical methods. The delivery catheter 12 can include conventional medical grade materials such as nylon, polyacrylamide, polycarbonate, polyethylene, polyformaldehyde, polymethylacrylate, polypropylene, polytetrafluoroethylene, polytrifluorochlorethylene, polyvinylchloride, polyurethane, elastomeric organosilicon polymers, Pebax® polyether block amide, and metals such as stainless steel and nitinol.

As shown in FIG. 1A, the occlusion device 14 includes a barrier member 30 that is generally impermeable to fluid flow therethrough. The occlusion device 14 may also include an attachment element 40 capable of retaining the barrier member 30 within a body lumen. In some embodiments, the barrier member 30 is oriented along the central longitudinal axis XL and includes a length L (FIG. 3A). In various examples, the barrier member 30 has a generally cylindrical cross-sectional configuration, having an inner diameter $D_1$ and an outer diameter $D_2$ (FIGS. 7A and 7B) when the occlusion device 14 is in the delivery configuration. The barrier member 30 may be in the form of a tubular sleeve or sheath. In some examples, the barrier member 30 is secured to the delivery catheter 12, such as a body 26 of the delivery catheter 12.

As discussed above, the attachment element 40 is configured to maintain the barrier member 30 against an inner wall 60 of the body lumen upon expansion of the barrier member 30 from the delivery configuration to the deployed configuration. In some embodiments, the attachment element 40 may be an anchor feature 42, as shown in FIG. 1B.

Figure 1B:
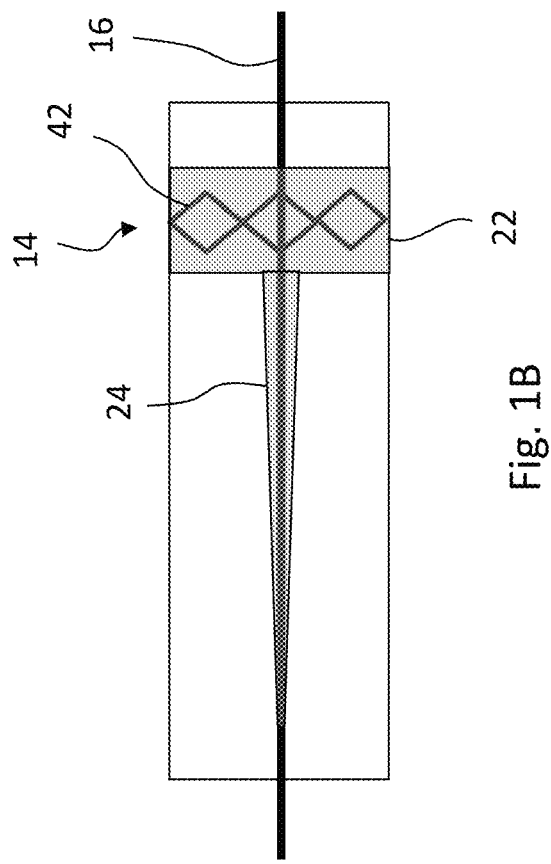
FIG. 1B shows a profile of an occlusion system in a deployed configuration, according to some embodiments.

FIG. 1B is an example of the device 14 in an expanded, or deployed configuration. As further described, the device 14 is expandable between the delivery configuration and the deployed configuration. For example, the occlusion device 14 may be self-expanding, balloon-expandable, or combinations thereof. As shown, following deployment, the device 14 includes an enlargeable portion 22, otherwise referred to as an engagement portion, having an inner diameter $D_1'$ and an outer diameter $D_2'$ (not shown) and a sealing portion, or tail portion 24. As described in further detail below, the tail portion 24 has a central lumen that is configured to self-seal under body pressure. For example, the tail portion 24 is optionally formed of a flexible or compliant material as subsequently discussed and is configured to collapse under back-pressure external to the tail portion 24. For example, fluid pressure on the upstream side of the attachment element 40 compresses the tail portion 24 into a flat or smashed configuration, sealing the barrier member 30 and preventing fluid flow therethrough.

FIGS. 2A-C show various examples of anchor features, according to some embodiments. In some embodiments, the anchor feature 42a may be, for example, a support member 44, as shown in FIG. 2A. The support member 44 includes a framework that is expandable upon application of a radial expansion force. For example, the support member 44 may be an expandable stent ring, a self-expanding stent, or a balloon expandable stent, among other things. In some embodiments, the support member 44 is expandable to a suitable size and/or shape to fit inside the body lumen at the desired treatment location. For example, the support member 44 may have a deployed diameter approximately equal to the inner diameter of the body lumen at the desired treatment location. The support member 44 may be formed of a variety of suitable and biocompatible materials such as various metallic and non-metallic materials, including shape-memory alloys, nitinol, stainless steels, expandable polymers, plastics, and other biocompatible metals.

FIG. 2B shows another embodiment of an anchor feature. The anchor feature 42 may also be, for example, a barb 42b. As shown in FIG. 2B, the barb 42b attaches to the inner wall of the body lumen and secures and/or seals the barrier member 30 at the desired treatment location. For example, the barb 42b may be any of a spike, spur, hook or other feature that catches the inner wall of the body lumen to secure the barrier member 30 at the desired treatment location.

In another example, shown in FIG. 2C, the anchor feature 42 is an adhesive material 42c, such as an adhesive strip or coating around an outer wall of the barrier member 30. Upon expansion of the barrier member 30, the adhesive material can adhere to an inner wall of the body lumen, thereby helping to secure and/or seal the barrier member 30 to the surrounding body lumen at the desired treatment location. In other embodiments, the enlargeable portion 22 of the barrier member 30 may simply comprise a stiffer or more rigid material, as compared to the tail portion 24, such that the enlargeable portion 22 is capable of forming to the inner wall of the body lumen. From the foregoing, it should be understood that a variety of anchor features 42 are contemplated, and that a combination of the foregoing examples (e.g., adhesive, barb, and/or support member combinations) may also be implemented.

FIGS. 3A-B show various examples of barrier members, according to some embodiments. In some embodiments, the barrier member 30 has a first end 32, a second end 34, a first portion 33 near the first end 32, a second portion 35 near the second end 34, and a lumen 36 extending from the first end 32 to the second end 34 along the central longitudinal axis XL. In some embodiments, the barrier member 30 is configured in a continuous, tubular or cylindrical shape as shown in FIG. 3A. For example, the barrier member 30 may be extruded, wrapped, or otherwise formed as a continuous tube. In some embodiments, the barrier member 30 may comprise features to promote collapsing or flattening of the tail portion 24. Such features may include, for example, creases, folds, seams, perforations, and laser cut lines, among other things. In some examples, the barrier member 30 may comprise one or more layers or sheets of material (e.g., film material) as shown in FIG. 3B. For example, the barrier member 30 can include a first sheet 38 adhered to a second sheet 39 to form a pair of longitudinal seams and a lumen 36. In other examples, the tail portion 24 of the barrier member 30 may include opposing, longitudinal creases to facilitate collapsing. As described in greater detail below, such an arrangement has lower resistance to collapsing under pressure (e.g., in comparison to a circular cross-section) and may facilitate more effective sealing.

In some examples, the length L of the barrier member 30 may be from about 5 cm to about 20 cm. However, the length may vary depending on a variety of factors, including the anatomy of the patient and the desired treatment location. The barrier member 30 may have an outer diameter $D_2$ suitable such that a ratio of the outer diameter $D_2$ to the length L is at least 1 to 10.

In one example, the barrier member 30 is elastomeric and configured to stretch. The barrier member 30 can comprise any suitable, expandable and biocompatible material. Examples of suitable materials include, for example, fluoropolymers (e.g., polytetrafluoroethylene), polyurethanes, polyether block amides, and various elastomeric organosilicone polymers such as polysiloxanes. In various examples, the barrier member 30 comprises a necking film formed of polytetrafluoroethylene, polyethylene, or other materials as desired. As described herein, the term "necking film" can be defined as a film or layer of material capable of deforming longitudinally and decreasing in cross-sectional area as a result of localized strain.

Figure 4:
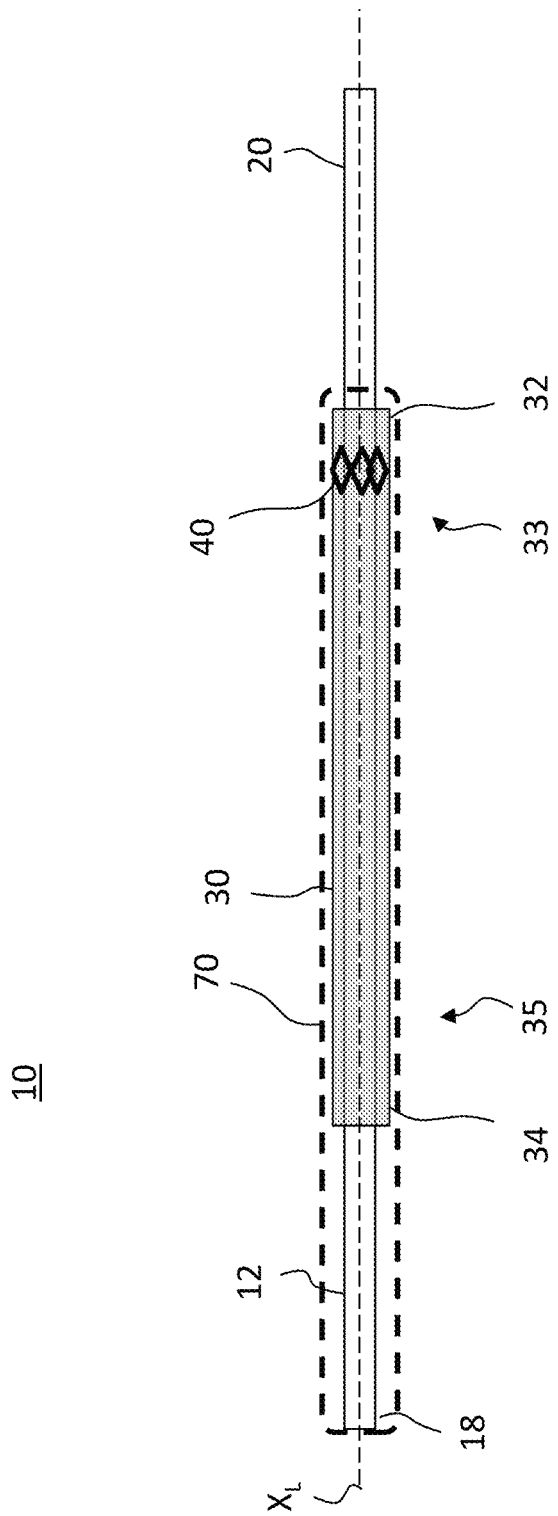
FIG. 4 shows a profile of a self-expanding occlusion system, according to some embodiments.

FIG. 4 shows a profile of a self-expanding occlusion system, according to some embodiments. In some embodiments, the occlusion system 10 may also include a constraint 70, otherwise referred to as a sheath or a sleeve, configured to prevent the device 14 from self-expanding before deployment is desired. As shown, the barrier member 30 may be removably coupled to the delivery catheter 12 (e.g., the body 26) at a first portion 33 and/or the first end 32. In some embodiments, at least the first portion 33 and/or the first end 32 of the barrier member 30 is expandable from the delivery configuration to the deployed configuration.

Figure 5:
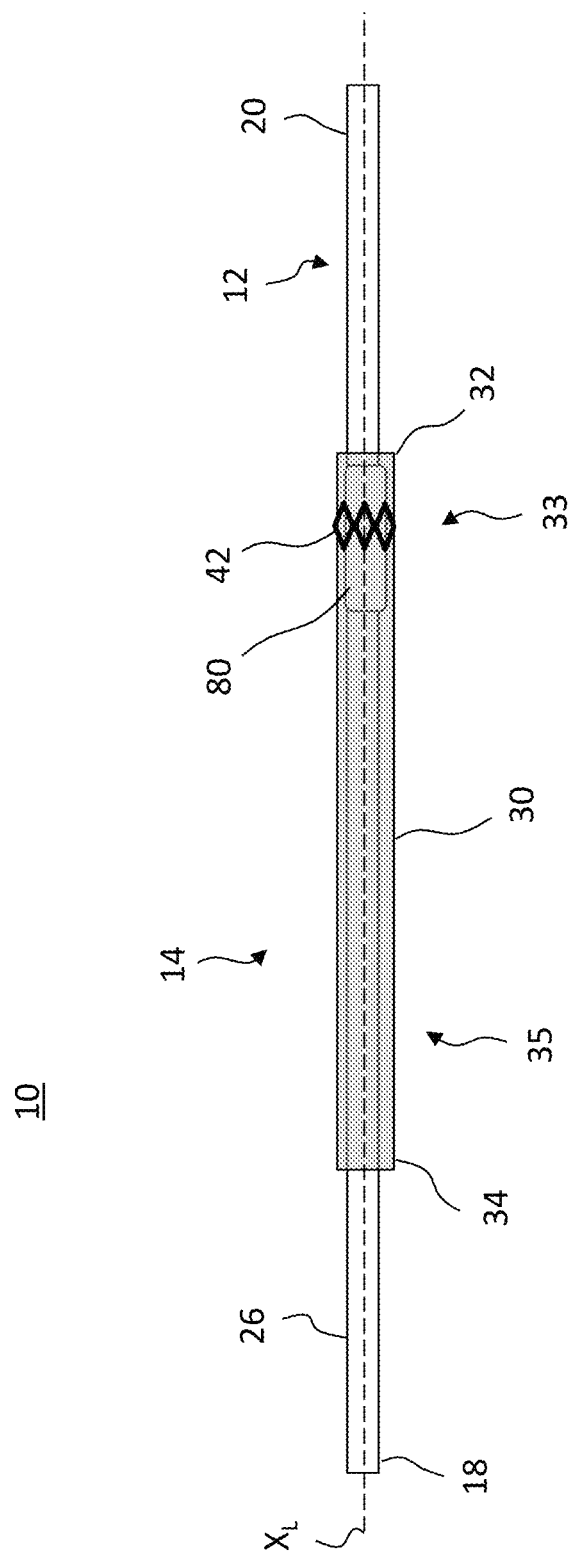
FIG. 5 shows a profile of a balloon-expandable occlusion system having a non-everted tail portion, according to some embodiments.

FIG. 5 shows a profile of a balloon-expandable occlusion system, according to some embodiments. As shown, the balloon 80 is operably coupled to the body 26 of the delivery catheter 12 such that the balloon 80 is capable of being diametrically adjusted to an enlarged diameter. In some examples, the device 14 is removably coupled to the balloon 80 and is configured to expand upon inflation of the balloon 80.

The balloon 80 may be located at any of a variety of locations along the body 26 of the catheter 12, generally including any point between the proximal end 18 and the distal end 20 of the catheter 12 as desired. In some embodiments, the barrier member 30 is removably coupled to the balloon 80 at the first portion 33 or the first end 32 of the barrier member 30, as shown in FIG. 5. The barrier member 30 can be coupled to the balloon 80 at any location along the working length of the balloon 80 as desired.

The balloon 80 can comprise a material that is generally inelastic and allows the balloon 80 to expand to a desired diameter upon sufficient pressurization. The balloon 80 can be formed of any of a variety of suitable, biocompatible materials. For example, suitable materials include nylon, polyethylene, polyethylene terephthalate (PET), polycaprolactam, polyesters, polyethers, polyamindes, polyurethanes, polyimides, acrylonitrile butadiene styrene (ABS) copolymers, polyester/polyether block copolymers, ionomer resins, liquid crystal polymers, rigid rod polymers, polyurethanes, latex, and elastomeric organosilicone polymers such as polysiloxanes.

Figure 6:
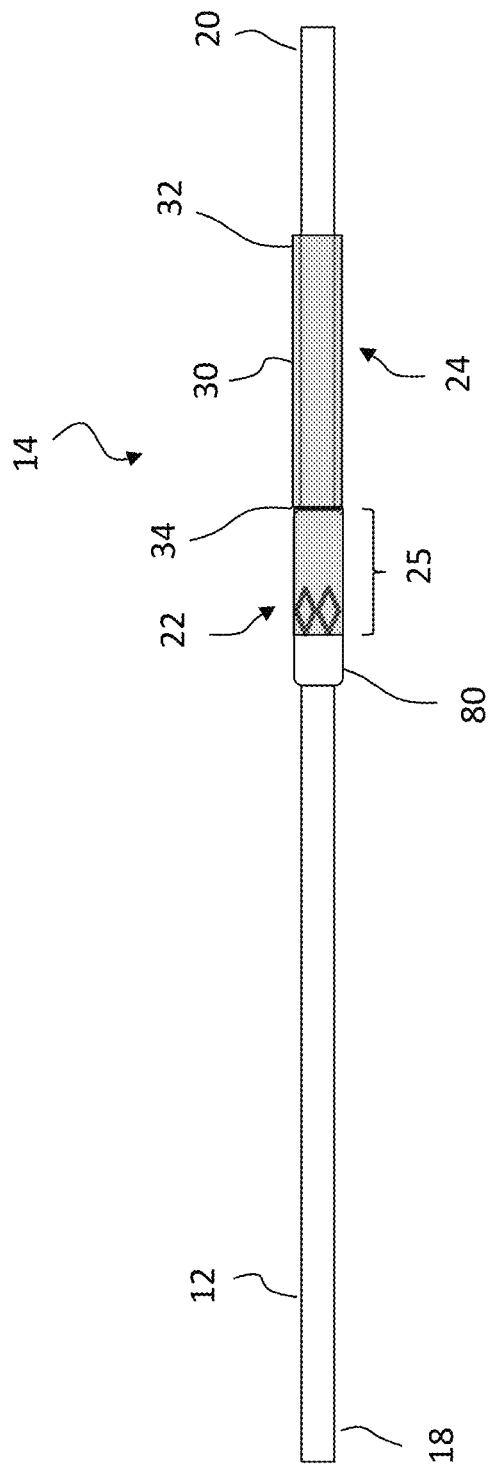
FIG. 6 shows a profile of a balloon-expandable occlusion system having an everted tail portion, according to some embodiments.

As shown in FIG. 6, in some examples, at least a portion of the barrier member 30 is overlapped onto itself (e.g., during an eversion process). For example, the tail portion 24 of the barrier member 30 is optionally everted to define an overlapped portion 25 and an everted length of material. As shown, both the first end 32 and the second end 34 of the barrier member 30 are oriented in the same direction (e.g., toward the distal end 20 of the delivery catheter 12). In some embodiments, the overlapped portion 25 may be shorter than the tail portion 24. The tail portion 24 may have a length from about 7 cm to about 25 cm or from about 10 cm to about 21 cm. However, the tail portion 24 may have any length as desired, which may depend on the desired treatment location.

In some embodiments, the first end 32 or the tail portion 24 of the barrier member 30 is optionally coupled or adhered to the body 26 of the delivery catheter 12 near the distal end 20 of the delivery catheter 12, allowing the first end 32 to be retracted proximally upon removal of the delivery catheter 12 from the patient's body. In some embodiments, the first end 32 or tail portion 24 is adhered to the delivery catheter 12 by way of an adhesive material (e.g., an adhesive strip on an inner wall of the lumen 36 of the barrier member 30). However, the first end 32 or tail portion 24 can be coupled to the delivery catheter 12 in a variety of other ways such as, for example, friction fits, thermal bonding, anchors, fasteners or other types of attachment as desired.

In some embodiments, the first end 32 or tail portion 24 of the barrier member 30 is configured to detach from the delivery catheter 12 by application of tension or a retraction force to the catheter following expansion of the enlargeable portion 22 of the barrier member 30. For example, the tail portion 24 may detach from the delivery catheter 12 upon retraction of the delivery catheter 12 from the patient's body. In some embodiments, the tail portion 24 of the barrier member 30 is configured to neck down or reduce in diameter during detachment from the delivery catheter 12. For example, the tail portion 24 may elastically recover a reduced diameter, or stretch or lengthen during detachment from the delivery catheter 12 to plastically deform to a smaller diameter, creating a smaller diameter at the first end 32 than at the second end 34.

In various examples, the tail portion 24 of the barrier member 30 is radially unsupported and is configured to collapse upon itself under pressure and close. The tail portion 24 may flatten or compress against itself under external pressure to create a seal. In some embodiments, the barrier member 30 flattens or compresses as a result of the fluid pressure (e.g., blood pressure) within the body lumen. For example, when deployed, the fluid pressure on a first side of the device 14 and exterior to the barrier member 30, and specifically the tail portion 24 of barrier member 30, may be higher than the fluid pressure on a second side of the device and within the barrier member 30, causing the tail portion 24 of the barrier member 30 to flatten or compress against itself.

In some embodiments, the tail portion 24 may collapse longitudinally (e.g., by "scrunching"). In some embodiments, the tail portion 24 may collapse diametrically, such as when tubular (e.g., FIG. 3A). In some embodiments, the barrier member 30 may collapse radially by flattening. For example, when formed with two opposing sides or sheets (e.g., FIG. 3B) secured together at opposing seams, the first sheet 39 and second sheet 41 may readily flatten against one another to close the lumen 36. As discussed above, the barrier member 30 may be creased, scored, pleated, folded, be formed with seams or otherwise treated to encourage repeatable collapse under pressure.

FIGS. 7A-D show a method of delivering the occlusion device 14 to the desired treatment area. Although the method discussed herein includes a balloon-expandable system, the method can also be employed for self-expanding systems or other systems.

Figure 7A:
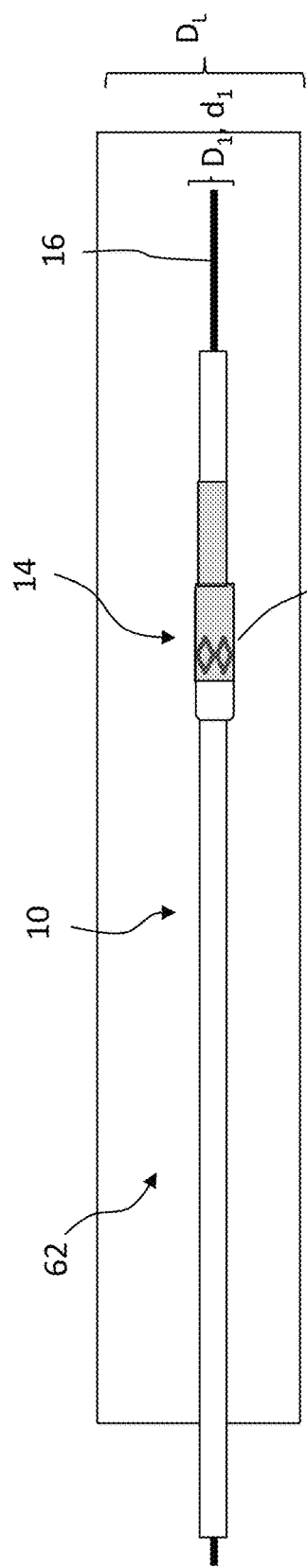
FIGS. 7A-7D show a method of delivering an occlusion device to a body lumen of a patient, according to some embodiments.

As shown in FIG. 7A, the occlusion system 10 is introduced into the body of a patient and guided along a guidewire 16 to the desired treatment area within a body lumen 62. As discussed above, the desired treatment area may be any of a vein, artery, gastrointestinal passageway, or other body passageway. The body lumen 62 includes an inner wall 60 having an inner diameter DL.

Figure 7B:
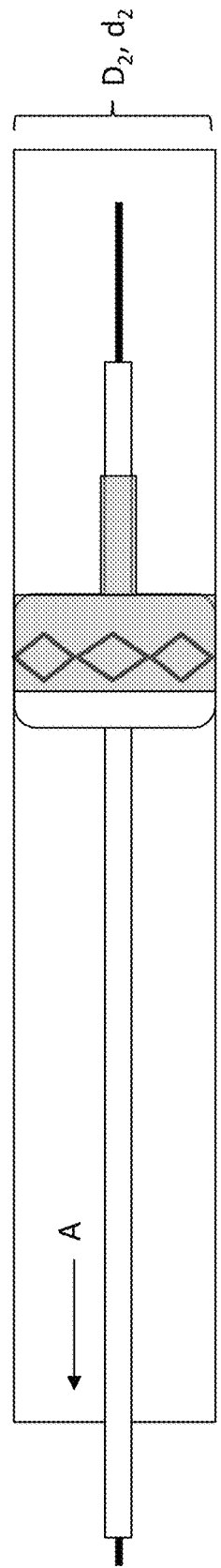

Once at the desired treatment location, at least the enlargeable portion 22 of the barrier member 30 is expanded from the delivery configuration (FIG. 7A) to the deployed configuration (FIG. 7B). As shown, the barrier member 30 and/or the anchor feature 42 are expanded via inflation of the balloon 80. However, as discussed above, the barrier member 30 and/or the anchor feature 42 may also be self-expanding upon removal of the constraint 70 (FIG. 4).

When in the deployed configuration, the barrier member 30 and the anchor feature 42 have deployed diameters approximately equal to the inner diameter DL of the body lumen 62. In some embodiments, wherein the anchor feature 42 is a support member 44, the support member 44 creates a pressure fit with the inner wall 60 of the body lumen 62 and maintains the barrier member 30 against the inner wall 60. Although shown in use with the support member 44, the system 10 can use a variety of anchor features 42 as described above. For example, the barrier member 30 can be maintained or attached to the inner wall 60 via barbs (FIG. 2B) and/or other anchoring mechanisms such as adhesive material (FIG. 2C).

The delivery catheter 12 is then retracted proximally from the body lumen 62 in the direction denoted by arrow A. In some embodiments, the second end 34 is pulled through the enlargeable portion 22 of the barrier member 30 and forms the tail portion 24 (FIG. 7C) oriented in the proximal direction. For example, the barrier member 30 is optionally everted back through the overlapped portion 25 and the support member 44 to form the tail portion 24. In some embodiments, the tail portion 24 is stretched and necked down or reduced in diameter as the delivery catheter 12 is retracted. In other embodiments, the tail portion 24 may neck down or reduce in diameter as the support member 44 is expanded from the delivery configuration to the deployed configuration. In yet other embodiments, the tail portion 24 flattens or compresses against itself to form a seal, as discussed above. The second end 34 or tail portion 24 of the barrier member 30 detaches from the delivery catheter 12 (e.g., via a shearing action between the deforming tail portion 24 and delivery catheter 12) as the delivery catheter 12 is removed from the body lumen 62 with the second end 34 of the barrier member 30 subsequently closing to form a seal.

Figure 7C:
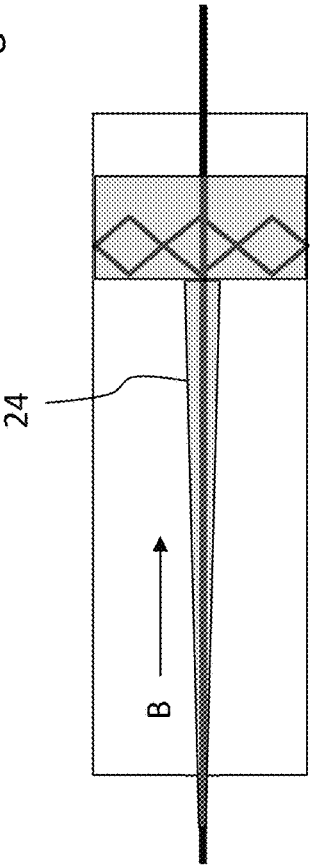
Figure 7D:
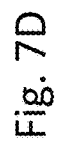

As shown in FIG. 7C, the tail portion 24 is oriented in the opposite direction of fluid flow (denoted by arrow B) through the body lumen 62 (i.e., upstream of the support member 44). As discussed above, the fluid pressure on the upstream side of the support member 44 compresses the tail portion 24 into a flat or smashed configuration as indicated in FIG. 7D, sealing the barrier member 30, preventing fluid flow therethrough and occluding the body lumen 62.

FIGS. 8A-D illustrate another embodiment in which the barrier member 30 is not everted as part of assembly to the delivery catheter 12. As shown, the barrier member 30 is similarly deployed but rather than everting the barrier member 30 to form the tail portion 24 via retraction of the delivery catheter 12, the tail portion 24 is simply pulled, necked down, and released from delivery catheter 12, after which the tail portion 24 is compressed by the blood pressure and self-seals.

FIG. 8A shows the occlusion system 10 introduced into the body of a patient and guided along a guidewire 16 to the desired treatment area within a body lumen 62. As discussed above, the desired treatment area may be any of a vein, artery, gastrointestinal passageway, or other body passageway.

Once at the desired treatment location, at least the enlargeable portion 22 of the barrier member 30 is expanded from the delivery configuration (FIG. 8A) to the deployed configuration (FIG. 8B). As shown, the barrier member 30 and/or the anchor feature 42 are expanded via inflation of the balloon 80. However, as discussed above, the barrier member 30 and/or the anchor feature 42 may also be self-expanding upon removal of the constraint 70.

The delivery catheter 12 is then retracted proximally from the body lumen 62 in the direction denoted by arrow A. In some embodiments, the second end 34 remains in the proximal direction (FIG. 8C). The tail portion 24 may then be stretched and necked down or reduced in diameter as the delivery catheter 12 is retracted through the barrier member 30. In other embodiments, the tail portion 24 may neck down or reduce in diameter as the support member 44 is expanded from the delivery configuration to the deployed configuration. In yet other embodiments, the tail portion 24 flattens or compresses against itself to form a seal, as discussed above.

As shown in FIG. 8C, the tail portion 24 is oriented in the opposite direction of fluid flow (denoted by arrow B) through the body lumen 62 (i.e., upstream of the support member 44). As discussed above, the fluid pressure on the upstream side of the support member 44 compresses the tail portion 24 into a flat or smashed configuration as indicated in FIG. 8D, sealing the barrier member 30, preventing fluid flow therethrough and occluding the body lumen 62.

FIGS. 9-11B show an occlusion device, as describe in detail above, deployed at various desired treatment locations. FIG. 9, for example, shows the occlusion device 14 employed within a body lumen of a patient, according to one embodiment. In such an example, the device 14 is used to occlude a hole, fenestration, or passageway (e.g., in a Fontan procedure) between a patient's heart H and inferior vena cava IVC.

Figure 10:
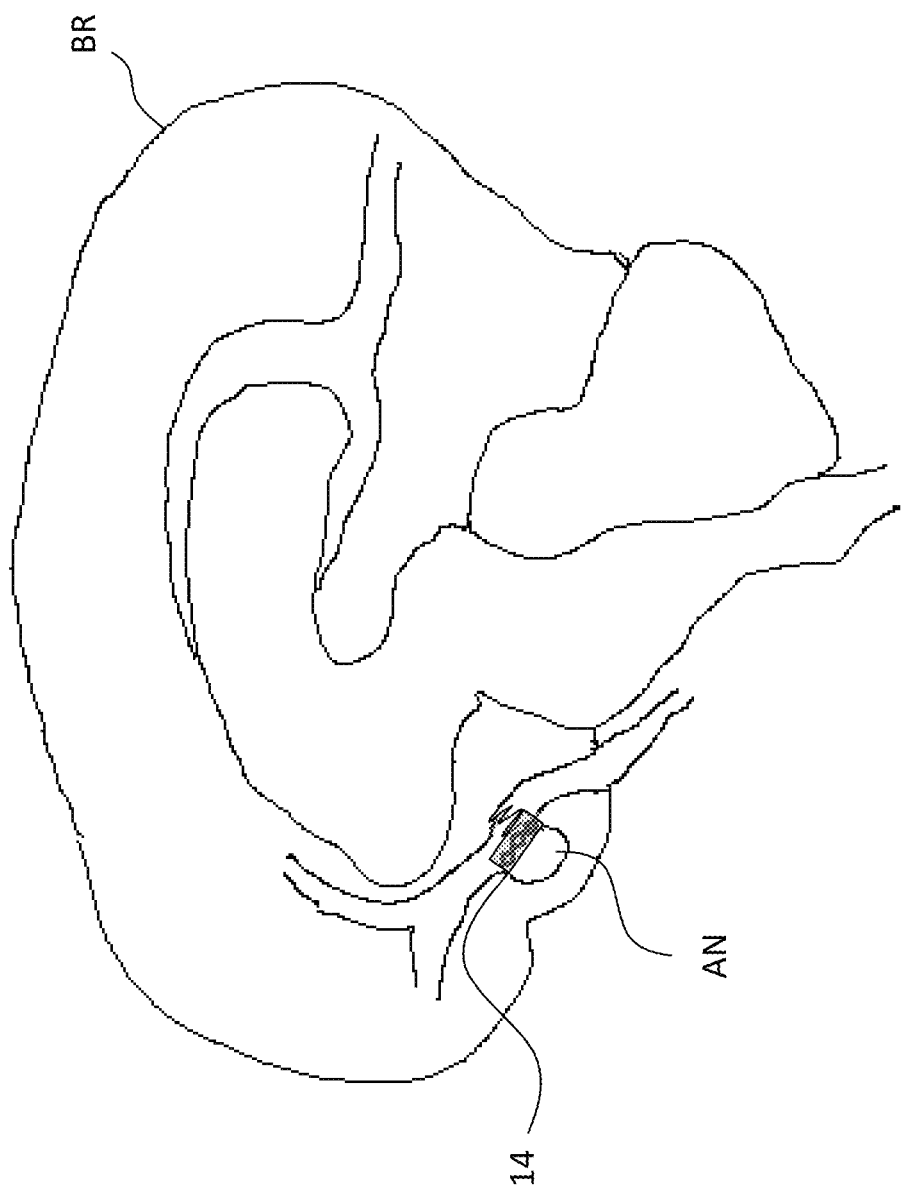
FIG. 10 is an example of an occlusion device employed within a body lumen of a patient, according to some embodiments.

In another example, shown in FIG. 10, the device 14 can be used to occlude various passageways in the brain BR to, for example, bypass or occlude an aneurysm AN.

Figure 11A:
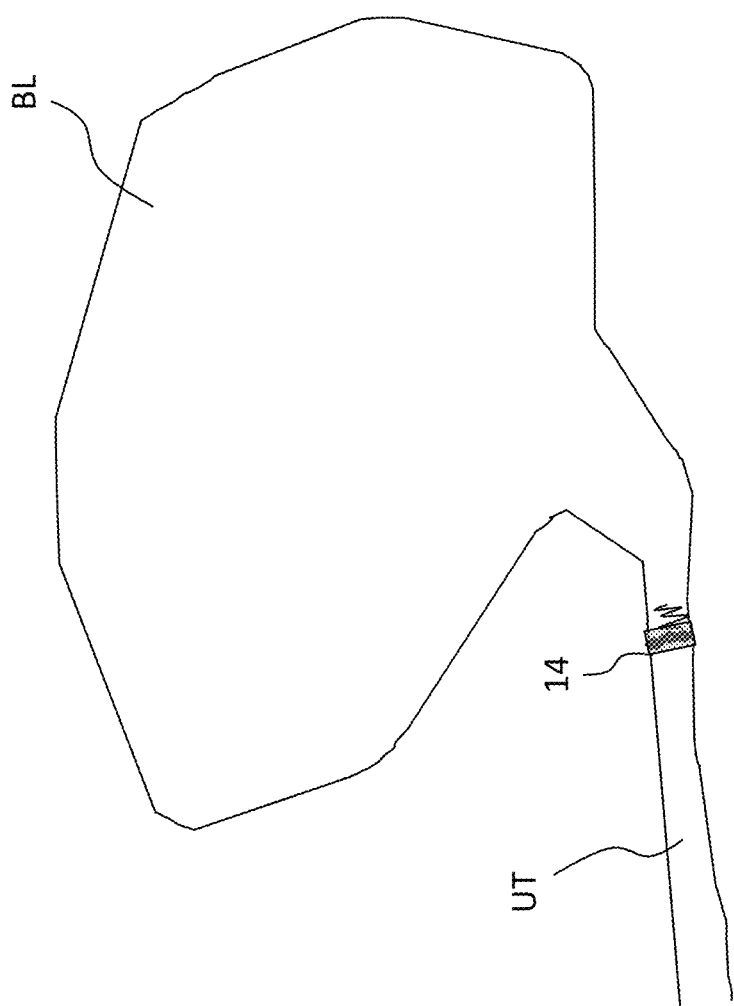
FIG. 11A is an example of an occlusion device employed within a body lumen of a patient, according to some embodiments.

In another example, shown in FIG. 11A, the device 14 can be used as an optional one-way valve. For example, the device 14 may be placed in a urinary tract UT (downstream of a patient's bladder BL) to mitigate and/or reduce the severity of certain conditions such as, for example, urinary incontinence. If fluid pressure drops on an upstream side of the device 14, the tail portion 24 (oriented on the upstream side of the device 14) may collapse upon itself and form a seal.

Figure 11B:
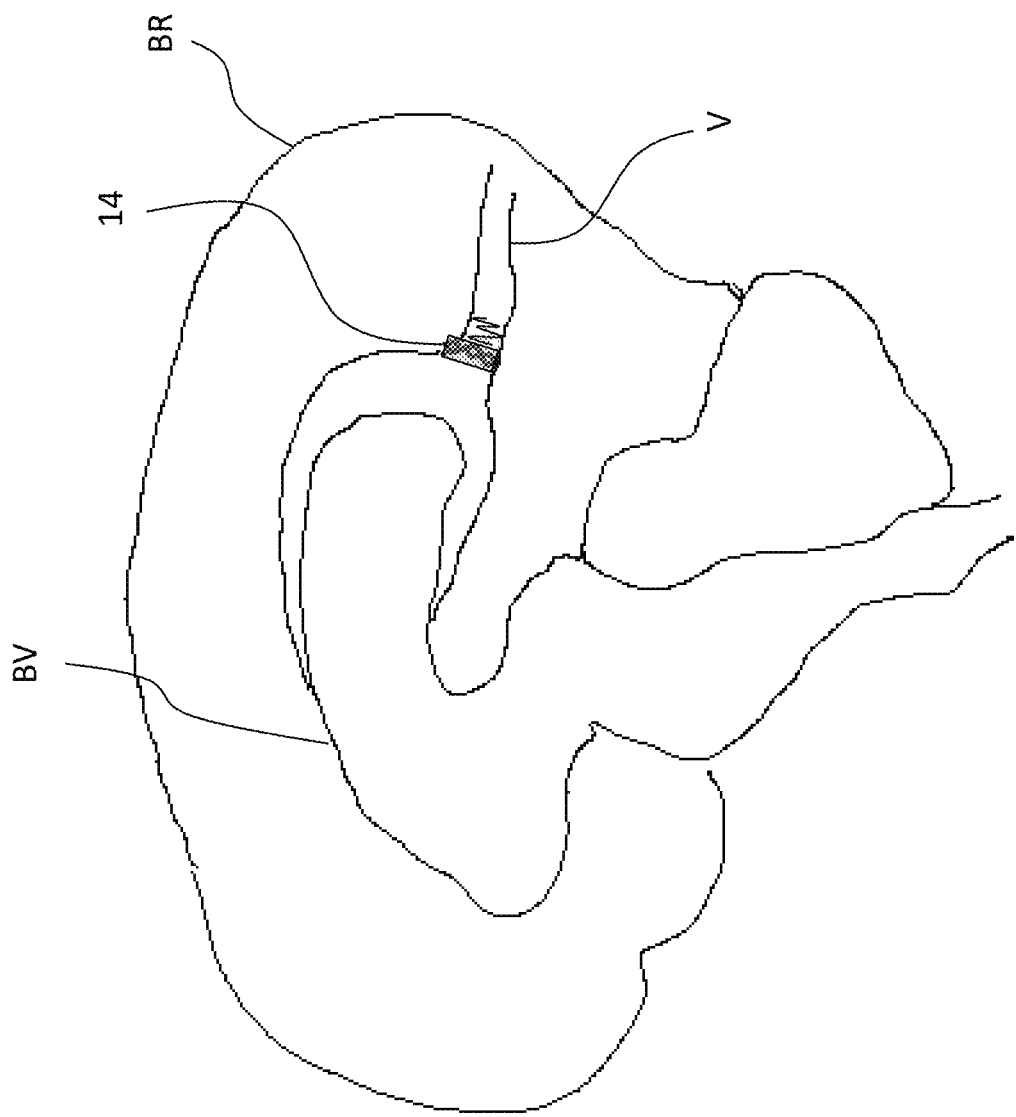
FIG. 11B is an example of an occlusion device employed within a body lumen of a patient, according to some embodiments.

In another example, shown in FIG. 11B, the device 14 can be used as a one-way relief valve for treating conditions such as hydrocephalus, in which cerebrospinal fluid builds up in the brain and must be occasionally relieved. In such examples, the device 14 may allow fluid flow in one direction (i.e., in the case of hydrocephalus, from a brain ventricle (BV) into the venous system (V)) if the fluid pressure on the upstream side of the device 14 exceeds the fluid pressure on the downstream side of the device 14 or the side of the device 14 in which the tail portion 24 is oriented. If fluid pressure on the downstream side of the device 14 exceeds pressure on the upstream side, the tail portion 24 may collapse upon itself and form a seal.

The examples that follow illustrate the performance of various designs consistent with the foregoing description. These examples should be read in an illustrative manner, and should no be read to limit the scope of the disclosure.

EXAMPLES

The following examples illustrate the correlation between everted tail length and amount of leakage for barrier members having varying diameters. The barrier members used in all examples had a starting length of 8 inches. The barrier members were comprised of ePTFE film capable of stretching and/or necking down from a starting diameter to a smaller, necked diameter upon eversion. After eversion, the barrier member was then placed inside of a plastic cylinder and the cylinder was filled with water to a pressure that simulated blood pressure in the human body. The barrier member was cut shorter after each sample run. For example, the barrier member was cut from 8 inches to 6 inches after the first sample run. Therefore, the same barrier member was used for each sample.

Example 1

The effect of everted tail length on leakage was observed for a barrier member having an original diameter of 0.050 inches (0.127 cm). The various water pressures and respective everted tail lengths of each sample are denoted in Table 1 below.

TABLE 1

| Sample | Water Pressure (in. $H_2O$) | Everted Tail Length (in.) | Observations |
| --- | --- | --- | --- |
| 1 | 36 | 8 | No leakage |
| 2 | 48 | 6 | No leakage |
| 3 | 48 | 4 | Trace leakage |
| 4 | 48 | 3 | Slow leakage |
| 5 | 48 | 2 | Moderate leakage |

As shown in Table 1, Samples 1 and 2 having an everted tail length of 8 inches (20.32 cm) and 6 inches (15.24 cm), respectively, exhibited no signs of visible leakage when subjected to a water pressure similar to that of blood pressure. Sample 3, having an everted tail length of 4 inches (10.16 cm), exhibited trace amounts of leakage. While Samples 4 and 5, having everted tail lengths of 3 inches (7.62 cm) and 2 inches (5.08 cm), respectively, exhibited slow to moderate leakage. Therefore, it was concluded that shorter everted tail lengths, specifically tail lengths of less than 4 inches (7.62 cm), exhibited a greater amount of leakage than longer everted tails.

Example 2

The effect of everted tail length on leakage was observed for a barrier member having a diameter of 0.100 inches (0.254 cm). The various water pressures and respective everted tail lengths of each sample are denoted in Table 2 below.

TABLE 2

| Sample | Water Pressure (in. $H_2O$) | Everted Tail Length (in.) | Observations |
| --- | --- | --- | --- |
| 6 | 48 | 6 | Slow leakage |
| 7 | 48 | 4 | Moderate leakage |
| 8 | 48 | 2 | Fast leakage |

As shown in Table 2, Sample 6 having an everted tail length of 6 inches (15.24 cm) exhibited slower leakage than Samples 7 and 8, having everted tail lengths of 4 inches (7.62 cm) and 2 inches (5.08 cm), respectively. Therefore, as concluded in Experiment 1, generally, longer everted tail lengths correlate to less and/or slower leakage and shorter everted tail lengths correlate to more and/or faster leakage.

When comparing Examples 1 and 2, it was concluded that a smaller diameter tube exhibited less leakage than a larger diameter tube having the same everted tail length. For example, Sample 2, having a diameter of 0.050 inches (0.127 cm) and a tail length of 6 inches (15.24 cm), exhibited less leakage than Sample 6, having the same tail length but a larger diameter of 0.100 inches (0.254 cm). Similarly, Examples 3 and 7 had the same tail length (4 inches), but Example 3 exhibited only trace amounts of leakage, while Example 7 exhibited moderate leakage.

As disclosed above, Examples 1 and 2 were conducted in a plastic cylinder with water used to simulate blood pressure. Since blood and other bodily fluids are generally more viscous than water, the everted tail is expected to leak less and/or slower than observed in Examples 1 and 2 above. Thus, samples where no leakage or only trace leakage was observed would be expected to ultimately occlude during use in the human body.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An occlusion system comprising:
   a delivery catheter having a proximal end, a distal end, a proximal portion, and a distal portion; and
   an occlusion device coupled to the delivery catheter with the occlusion device in a reduced profile delivery configuration, the occlusion device including:
      a barrier member including a radially enlargeable portion, the radially enlargeable portion having a first length defining a first lumen portion,
      a tail portion extending from the enlargeable portion and having a second length defining a second lumen portion in communication with the first lumen portion, wherein the second length is greater than the first length,
      an anchor feature arranged with the enlargeable portion of the barrier member, wherein the first lumen portion extends through the enlargeable portion and the anchor feature and is configured to receive the delivery catheter, the enlargeable portion and the tail portion being releasably coupled to the catheter such that the tail portion is radially unsupported and the second lumen portion is collapsible upon deployment from the delivery catheter.

2. The system of claim 1, wherein the anchor feature includes a support member coupled to the enlargeable portion of the barrier member, the support member being expandable from a delivery configuration to a deployed configuration.

3. The system of claim 1, wherein the tail portion of the barrier member is configured to be pulled, necked down, and released from the delivery catheter upon application of a retraction force to the tail portion with the catheter.

4. The system of claim 1, wherein the tail portion is configured to plastically deform and neck down in diameter upon application of the retraction force on the tail portion prior to release of the tail portion from the catheter.

5. The system of claim 1, wherein the tail portion includes opposing, longitudinal creases configured to facilitate radial collapsing of the tail portion following release from the catheter.

6. The system of claim 1, wherein the tail portion is adhered to the catheter.

7. The system of claim 1, wherein the tail portion is formed of an elastomeric material and is configured to constrict following release from the delivery catheter.

8. The system of claim 1, wherein a ratio of an outer diameter of the barrier member to a total length of the barrier member is at least 1 to 10.

9. The system of claim 1, wherein the tail portion is configured to evert through the enlargeable portion during retraction of the catheter following deployment of the enlargeable portion.

10. The system of claim 1, wherein the anchor feature includes at least one of: adhesive, one or more barbs, and an expandable framework.

11. The system of claim 1, further comprising a balloon configured to expand the enlargeable portion from the delivery configuration to the deployed configuration upon inflation of the balloon.

12. The system of claim 1, further comprising a constraint configured to prevent expansion of the enlargeable portion prior to deployment.

13. The system of claim 1, wherein the occlusion device is releasably coupled to the catheter with the first lumen portion and the second lumen portion received over the catheter.

14. An implantable medical device, comprising:
a barrier member having a first end, a second end, an enlargeable portion with a first length configured to expand from a delivery configuration to a deployed configuration, a tail portion with a second length greater than the first length, a lumen extending through each of the enlargeable portion and the tail portion from the first end to the second end, a total length, and an outer diameter, wherein the tail portion of the lumen is configured to flatten against itself to form a seal; and
an anchor feature coupled to the barrier member at the enlargeable portion, the anchor feature configured to expand with the barrier member from the delivery configuration to the deployed configuration.

15. The device of claim 14, wherein a ratio of the outer diameter of the barrier member to the length of the barrier member is at least 1 to 10.

16. The device of claim 14, wherein the anchor feature includes at least one of: adhesive, one or more barbs, and an expandable framework.

17. The device of claim 14, wherein the anchor feature comprises a support member having an expandable framework.

18. The device of claim 14, wherein the first end and the second end of the barrier member are substantially open while the enlargeable portion is in the delivery configuration.

19. The device of claim 14, wherein the second end of the barrier member is substantially closed while the enlargeable portion is in the deployed configuration.

20. The device of claim 14, wherein the tail portion of the barrier member is configured to evert upon expansion of the enlargeable portion to the deployed configuration.

21. An implantable medical device comprising:
a barrier member including a radially enlargeable portion, the radially enlargeable portion having a first length defining a first lumen portion,
a tail portion extending from the enlargeable portion and having a second length defining a second lumen portion in communication with the first lumen portion, wherein the second length is greater than the first length and the tail portion is configured to evert through the radially enlargeable portion and flatten against itself to form a seal.

* * * * *